United States Patent
Clifford et al.

(10) Patent No.: US 9,636,258 B2
(45) Date of Patent: *May 2, 2017

(54) SYSTEM AND METHOD FOR TREATMENT OF NON-VENTILATING MIDDLE EAR BY PROVIDING A GAS PATHWAY THROUGH THE NASOPHARYNX

(71) Applicant: Acclarent, Inc., Menlo Park, CA (US)

(72) Inventors: Anton G. Clifford, Mountain View, CA (US); Joshua Makower, Los Altos, CA (US); John Y. Chang, Los Altos, CA (US); John H. Morriss, San Francisco, CA (US); Earl A. Bright, II, Los Altos, CA (US); Eric Goldfarb, Belmont, CA (US); Julia D. Vrany, Los Altos, CA (US); Ketan P. Muni, San Jose, CA (US); William E. Bolger, Bethesda, MD (US); Joseph Roberson, Palo Alto, CA (US)

(73) Assignee: Acclarent, Inc., Irvine, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 14/722,300

(22) Filed: May 27, 2015

(65) Prior Publication Data
US 2015/0366716 A1    Dec. 24, 2015

Related U.S. Application Data

(63) Continuation of application No. 13/887,618, filed on May 6, 2013, now Pat. No. 9,072,626, which is a
(Continued)

(51) Int. Cl.
*A61F 2/18*    (2006.01)
*A61F 11/00*    (2006.01)

(52) U.S. Cl.
CPC ................................. *A61F 11/002* (2013.01)

(58) Field of Classification Search
CPC ....... A61F 2/18; A61F 2002/183; A61F 11/00
(Continued)

(56) References Cited

U.S. PATENT DOCUMENTS

| 1,080,934 A | 12/1913 | Shackleford |
| 1,200,267 A | 10/1916 | Sunnergren |

(Continued)

FOREIGN PATENT DOCUMENTS

| CH | 668188 | 12/1988 |
| CN | 2151720 | 1/1994 |

(Continued)

OTHER PUBLICATIONS

Argon Medical. Maxxim Medical. Ad for Sniper EliteTM Hydrophilic Ni—Ti Alloy Guidewire (2001).
(Continued)

*Primary Examiner* — Suzette J Gherbi
(74) *Attorney, Agent, or Firm* — Frost Brown Todd LLC

(57) ABSTRACT

Methods and devices for providing a gas pathway between the nasopharynx and the Eustachian tube are provided. One device may include a lumen with a valve. A portion of the valve may be tethered to adjacent muscle. Another portion of the valve may be tethered to adjacent cartilage. When the muscle contracts the valve may open through movement of the tethers, and provide a gas pathway between the nasopharynx and the Eustachian tube.

20 Claims, 12 Drawing Sheets

Related U.S. Application Data continuation of application No. 12/730,492, filed on Mar. 24, 2010, now Pat. No. 8,435,290.

(60) Provisional application No. 61/165,448, filed on Mar. 31, 2009.

(58) Field of Classification Search
USPC .......................................................... 623/10
See application file for complete search history.

(56) References Cited

U.S. PATENT DOCUMENTS

| | | |
|---|---|---|
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,525,183 A | 3/1947 | Robinson |
| 2,493,326 A | 1/1950 | Trinder |
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |

(56) References Cited

U.S. PATENT DOCUMENTS

| | | |
|---|---|---|
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Shockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wttermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |

(56) References Cited

U.S. PATENT DOCUMENTS

| | | |
|---|---|---|
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterwreck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hedge et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,277,148 B1 * | 8/2001 | Dormer .............. A61F 2/18 600/25 |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |

(56) References Cited

U.S. PATENT DOCUMENTS

| | | |
|---|---|---|
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,145,659 B2 | 12/2006 | Yasuda et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |

(56) References Cited

U.S. PATENT DOCUMENTS

| | | |
|---|---|---|
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,799,048 B2 | 9/2010 | Hudson et al. |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,951,133 B2 | 5/2011 | Eaton et al. |
| 7,988,705 B2 | 8/2011 | Galdonik et al. |
| 7,993,353 B2 | 8/2011 | Rossner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,147,545 B2 | 4/2012 | Avior |
| 8,167,821 B2 | 5/2012 | Sharrow |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,435,290 B2 * | 5/2013 | Clifford ............... A61F 11/002 128/898 |
| 8,439,687 B1 | 5/2013 | Morriss et al. |
| 9,072,626 B2 * | 7/2015 | Clifford ............... H01S 5/0602 |
| 2001/0004644 A1 | 6/2001 | Levin |
| 2001/0034530 A1 | 10/2001 | Malackowski et al. |
| 2001/0051761 A1 | 12/2001 | Khadem |
| 2002/0006961 A1 | 1/2002 | Katz et al. |
| 2002/0055746 A1 | 5/2002 | Burke et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0063973 A1 | 3/2006 | Makower et al. |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2007/0020196 A1 | 1/2007 | Pipkin et al. |
| 2007/0112358 A1 | 5/2007 | Abbott |
| 2007/0129751 A1 | 6/2007 | Muni et al. |

(56) References Cited

U.S. PATENT DOCUMENTS

| | | |
|---|---|---|
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0183128 A1 | 7/2008 | Morriss et al. |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1* | 12/2009 | Goldfarb ............... A61M 29/02 604/514 |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0174308 A1 | 7/2010 | Chang et al. |
| 2010/0198191 A1* | 8/2010 | Clifford .................. A61B 1/227 604/514 |
| 2010/0198302 A1 | 8/2010 | Shalev |
| 2010/0274188 A1 | 10/2010 | Chang et al. |
| 2010/0290244 A1 | 11/2010 | Nath |
| 2011/0166190 A1 | 7/2011 | Anderson et al. |
| 2013/0245608 A1* | 9/2013 | Muni ..................... A61B 17/24 604/514 |

FOREIGN PATENT DOCUMENTS

| | | |
|---|---|---|
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | S 53-67935 | 6/1978 |
| JP | H 10-24098 | 1/1989 |
| JP | H 03-503011 | 7/1991 |
| JP | H 03-504935 | 10/1991 |
| JP | H 04-221313 | 8/1992 |
| JP | H 05-211985 | 8/1993 |
| JP | H 06-277296 | 10/1994 |
| JP | H 07-327916 | 12/1995 |
| JP | H 08-317989 | 12/1996 |
| JP | H 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 96/29071 | 9/1996 |
| WO | WO 97/21461 | 6/1997 |
| WO | WO 99/24106 | 5/1999 |
| WO | WO 99/30655 | 6/1999 |
| WO | WO 99/32041 | 7/1999 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |

(56) References Cited

FOREIGN PATENT DOCUMENTS

| WO | WO 2008/051918 | 5/2008 |
|---|---|---|
| WO | WO 2008/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter—Balloon Catheter—Thomas Fogarty. Www.inventors.about.com/library/inventors/blcatheter.htm?p=1.
Benninger et al.; Adult Chronic Rhinosinusitis: Defintions, Diagnosis, Epidemiology, and Pathophysilogy Arch Otolarygol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillumination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery', Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers—General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolaryngology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elesvier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE. (Mar. 2001).
Gottmann, et al. 'Successful treatment of Recurrent Post-Operative Frontal Sinus Stenoses by Balloon Dilatation' CIRSE. (Oct. 5, 2002).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.

(56) References Cited

OTHER PUBLICATIONS

Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa.Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splints Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa In the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com-MicroFrance Catalog Browser. Www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.

Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park, K. et al. 'Biodegradable Hydrogels for Drug Delivery' (1993) Technomic Publishing Inc. Lancaster.
Peirs, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Piccirillo, J.F. et al. 'Physchometric and Clinimetric Validity of the 20-Item Sino-Nasal Outcome test (SNOT-20)' Copyright 1996 Washington University, St. Louis, MO.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems. Www.dymax.com/products/curing_equipment/lightguids/light. (2004) pp. 1-2.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.

(56) References Cited

OTHER PUBLICATIONS

St. Croix, et al., 'Genes Expressed in Human Tumor Endothelium' Science (May 15, 2000) vol. 289 pp. 1197-1202.
Stammberger, H. 'Komplikationen entzundlicher Nasen-nebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al. 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
European Communication dated Sep. 4, 2008 for Application No. EP 05773189.
European Communication dated Jun. 19, 2009 for Application No. EP 05773189.
European Exam Report dated Feb. 22, 2006 for Application No. EP 02716734.5.
European Exam Report dated Feb. 8, 2007 for Application No. EP 02716734.5.
European Search Report and Written Opinion dated Sep. 27, 2011 for Application No. EP 10182961.
European Search Report and Written Opinion dated Sep. 29, 2011 for Application No. EP 10182893.
Partial European Search Report dated Sep. 20, 2007 for Application No. EP 07252018.
Partial European Search Report dated Mar. 25, 2008 for Application No. EP 07252018.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jun. 2, 2008 for Application No. EP 05773189.
Supplemental European Search Report and Written Opinion dated Sep. 11, 2009 for Application No. EP 06815174.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
International Preliminary Report on Patentability dated Aug. 7, 2006 for Application No. PCT/US2005/25371.
International Preliminary Report on Patentability and Written Opinion dated Sep. 25, 2007 for Application No. PCT/US2006/002004.
International Preliminary Report on Patentability and Written Opinion dated Nov. 18, 2008 for Application No. PCT/US2007/11449.
International Preliminary Report on Patentability and Written Opinion dated Apr. 7, 2009 for Application No. PCT/US2007/021170.
International Preliminary Report on Patentability and Written Opinion dated May 5, 2009 for Application No. PCT/US2006/036960.
International Preliminary Report on Patentability and Written Opinion dated Oct. 13, 2009 for Application No. PCT/US2008/059786.
International Preliminary Report on Patentability and Written Opinion dated Oct. 27, 2009 for Application No. PCT/US2008/061343.
International Search Report dated Jun. 3, 2002 for Application No. PCT/EP02/001228.
International Search Report and Written Opinion dated Apr. 10, 2006 for Application No. PCT/US2005/25371.
International Search Report and Written Opinion dated May 8, 2007 for Application No. PCT/US2006/016026.
International Search Report and Written Opinion dated Aug. 17, 2007 for Application No. PCT/US2005/013617.
International Search Report and Written Opinion dated Aug. 29, 2007 for Application No. PCT/US2006/002004.
International Search Report and Written Opinion dated Sep. 25, 2007 for Application No. PCT/US2006/037167.
International Search Report and Written Opinion dated Oct. 19, 2007 for Application No. PCT/US2007/003394.
International Search Report and Written Opinion dated May 29, 2008 for Application No. PCT/US2007/021170.
International Search Report and Written Opinion dated May 29, 2008 for Application No. PCT/US2007/021922.
International Search Report and Written Opinion dated Jul. 1, 2008 for Application No. PCT/US2006/022745.

(56) References Cited

OTHER PUBLICATIONS

International Search Report and Written Opinion dated Jul. 3, 2008 for Application No. PCT/US2006/029695.
International Search Report and Written Opinion dated Jul. 7, 2008 for Application No. PCT/US2007/016213.
International Search Report and Written Opinion dated Jul. 8, 2008 for Application No. PCT/US2007/011474.
International Search Report and Written Opinion dated Jul. 17, 2008 for Application No. PCT/US2006/036960.
International Search Report and Written Opinion dated Jul. 21, 2008 for Application No. PCT/US2005/033090.
International Search Report and Written Opinion dated Aug. 25, 2008 for Application No. PCT/US2008/000911.
International Search Report and Written Opinion dated Sep. 10, 2008 for Application No. PCT/US2007/016212.
International Search Report and Written Opinion dated Sep. 12, 2008 for Application No. PCT/US2007/016214.
International Search Report and Written Opinion dated Sep. 17, 2008 for Application No. PCT/US2008/059786.
International Search Report and Written Opinion dated Sep. 17, 2008 for Application No. PCT/US2008/061343.
International Search Report and Written Opinion dated Oct. 1, 2008 for Application No. PCT/US2007/011449.
International Search Report and Written Opinion dated Oct. 15, 2008 for Application No. PCT/US2008/061048.
International Search Report and Written Opinion dated Nov. 30, 2009 for Application No. PCT/US2009/057203.
International Search Report and Written Opinion dated Dec. 10, 2009 for Application No. PCT/US2009/052236.
International Search Report and Written Opinion dated Dec. 16, 2009 for Application No. PCT/US2009/050800.
International Search Report and Written Opinion dated Mar. 31, 2010 for Application No. PCT/US2009/069143.
International Search Report and Written Opinion dated Jul. 8, 2010 for Application No. PCT/US2010/027837.
International Search Report and Written Opinion dated Oct. 6, 2010 for Application No. PCT/US2010/040548.
International Search Report and Written Opinion dated Mar. 25, 2011 for Application No. PCT/US2010/062161.
International Search Report and Written Opinion dated Mar. 28, 2011 for Application No. PCT/US2010/061850.
International Search Report and Written Opinion dated Mar. 31, 2011 for Application No. PCT/US2010/060898.
International Search Report and Written Opinion dated Aug. 9, 2011 for Application No. PCT/US2011/038751.
International Search Report and Written Opinion dated May 18, 2012 for Application No. PCT/US2011/052321.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
U.S. Appl. No. 11/789,705, filed Apr. 24, 2007.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 61/165,448, filed Mar. 31, 2009.

\* cited by examiner

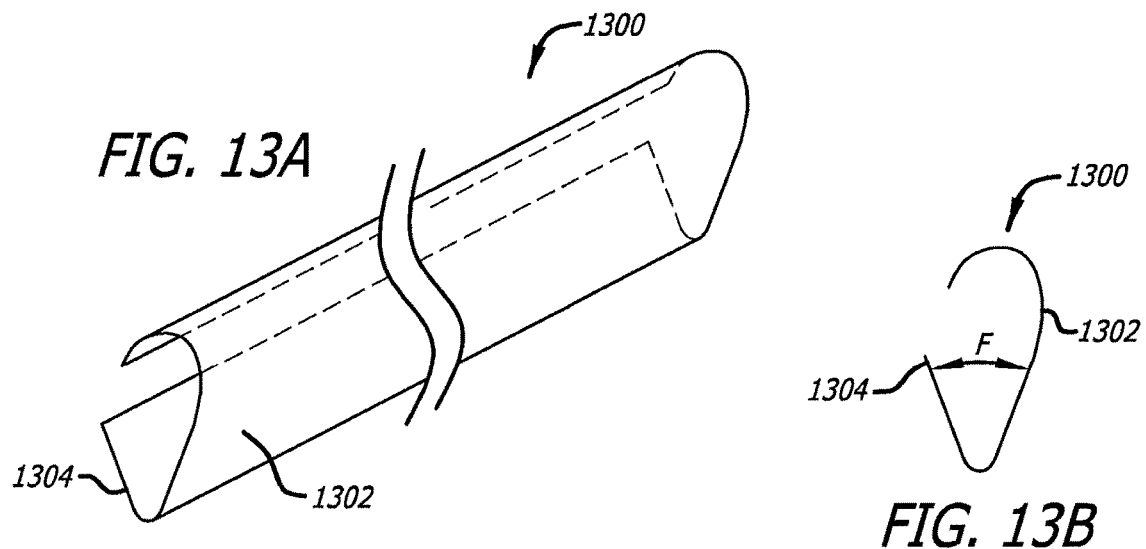
FIG. 13A
FIG. 13B
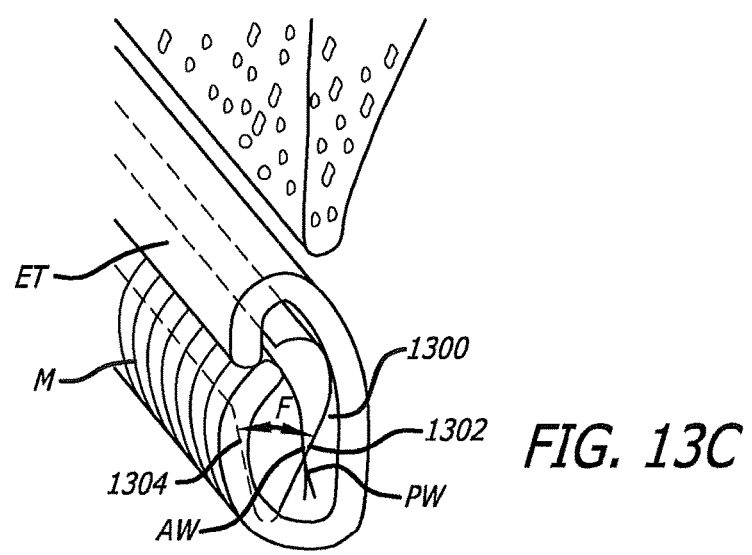
FIG. 13C

SYSTEM AND METHOD FOR TREATMENT OF NON-VENTILATING MIDDLE EAR BY PROVIDING A GAS PATHWAY THROUGH THE NASOPHARYNX

CROSS-REFERENCES TO RELATED APPLICATIONS

This application is a continuation of U.S. patent application Ser. No. 13/887,618, filed May 6, 2013 (now U.S. Pat. No. 9,072,626), which is a continuation of U.S. patent application Ser. No. 12/730,492, filed Mar. 24, 2010 (now U.S. Pat. No. 8,435,290), which claims the benefit of U.S. Provisional Patent Application Ser. No. 61/165,448, filed Mar. 31, 2009, the full disclosure of which is hereby incorporated by reference.

BACKGROUND OF THE INVENTION

The present invention is related to methods and systems for accessing, diagnosing and/or treating target tissue regions within the middle ear and the Eustachian tube.

Referring to FIGS. 1-2, the ear 10 is divided into three parts: an external ear 12, a middle ear 14 and an inner ear 16. The external ear 12 consists of an auricle 18 and ear canal 20 that gather sound and direct it towards a tympanic membrane 22 (also referred to as the eardrum) located at an inner end 24 of the ear canal 20. The middle ear 14 lies between the external and inner ears 12 and 16 and is connected to the back of the throat by a Eustachian tube 26 which serves as a pressure equalizing valve between the ear 10 and the sinuses. The Eustachian tube 26 terminates in a distal opening 28 in the nasopharynx region 30 of the throat 32. In addition to the eardrum 22, the middle ear 14 also consists of three small ear bones (ossicles): the malleus 34 (hammer), incus 36 (anvil) and stapes 38 (stirrup). These bones 34-38 transmit sound vibrations to the inner ear 16 and thereby act as a transformer, converting sound vibrations in the canal 20 of the external ear 12 into fluid waves in the inner ear 16. These fluid waves stimulate several nerve endings 40 that, in turn, transmit sound energy to the brain where it is interpreted.

The Eustachian tube 26 is a narrow, one-and-a-half inch long channel connecting the middle ear 14 with the nasopharynx 30, the upper throat area just above the palate, in back of the nose. The Eustachian tube 26 functions as a pressure equalizing valve for the middle ear 14 which is normally filled with air. When functioning properly, the Eustachian tube 26 opens for a fraction of a second periodically (about once every three minutes) in response to swallowing or yawning. In so doing, it allows air into the middle ear 14 to replace air that has been absorbed by the middle ear lining (mucous membrane) or to equalize pressure changes occurring on altitude changes. Anything that interferes with this periodic opening and closing of the Eustachian tube 26 may result in hearing impairment or other ear symptoms.

Obstruction or blockage of the Eustachian tube 26 results in a negative middle ear pressure 14, with retraction (sucking in) of the eardrum 22. In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear 14, creating a condition we call serous otitis media (fluid in the middle ear). This occurs frequently in children in connection with an upper respiratory infection and accounts for the hearing impairment associated with this condition.

A lining membrane (mucous membrane) of the middle ear 14 and Eustachian tube 26 is connected with, and is the same as, the membrane of the nose 42, sinuses 44 and throat 32. Infection of these areas results in mucous membrane swelling which in turn may result in obstruction of the Eustachian tube 26. This is referred to as serous otitis media, i.e., essentially a collection of fluid in the middle ear 14 that can be acute or chronic, usually the result of blockage of the distal opening 28 of the Eustachian tube 26 which allows fluid to accumulate in the middle ear 14. In the presence of bacteria, this fluid may become infected leading to an acute suppurative otitis media (infected or abscessed middle ear). When infection does not develop, the fluid remains until the Eustachian tube 26 again begins to function normally, at which time the fluid is absorbed or drains down the tube into the throat 32 through the Eustachian tube opening 28.

Chronic serous otitis media may result from longstanding Eustachian tube blockage, or from thickening of the fluids so that it cannot be absorbed or drained down the Eustachian tube 26. This chronic condition is usually associated with hearing impairment. There may be recurrent ear pain, especially when the individual catches a cold. Fortunately, serous otitis media may persist for many years without producing any permanent damage to the middle ear mechanism. The presence of fluid in the middle ear 14, however, makes it very susceptible to recurrent acute infections. These recurrent infections may result in middle ear damage.

When the Eustachian tube 26 contains a build-up of fluid, a number of things will occur. First, the body absorbs the air from the middle ear 14, causing a vacuum to form which tends to pull the lining membrane and ear drum 22 inward causing pain. Next, the body replaces the vacuum with more fluid which tends to relieve the pain, but the patient can experience a fullness sensation in the ear 10. Treatment of this condition with antihistamines and decongestants can take many weeks to be fully effective. Finally, the fluid can become infected which is painful and makes the patient feel ill and may not be able to hear well. If the inner ear 14 is affected, the patient may feel a spinning or turning sensation (vertigo). The infection is typically treated with antibiotics.

However, even if antihistamines, decongestants and antibiotics are used to treat an infection or other cause of fluid build-up in the middle ear 14, these treatments will typically not immediately resolve the pain and discomfort caused by the buildup of fluid in the middle ear 14, i.e., the most immediate relief will be felt by the patient if the fluid can be removed from the Eustachian tube 26.

Antibiotic treatment of middle ear infections typically results in normal middle ear function within three to four weeks. During the healing period, the patient can experience varying degrees of ear pressure, popping, clicking and fluctuation of hearing, occasionally with shooting pain in the ear. Resolution of the infection occasionally leaves the patient with uninfected fluid in the middle ear 14, localized in the Eustachian tube 26.

Fluid build-up caused by these types of infections has been treated surgically in the past. The primary objective of surgical treatment of chronic serous otitis media is to reestablish ventilation of the middle ear, keeping the hearing at a normal level and preventing recurrent infection that might damage the eardrum membrane and middle ear bones.

For example, as shown in FIG. 3, a myringotomy can be performed to relieve fluid in the middle ear 14. A myringotomy is an incision 42 in the eardrum 22 performed to remove fluid in the middle ear 14. A hollow plastic tube 44, referred to as a ventilation tube, is inserted and lodged in the incision 42 to prevent the incision 42 from healing and to insure ventilation of the middle ear 14. The ventilation tube 44 temporarily takes the place of the Eustachian tube 26 in equalizing the pressure in the middle ear 14. The ventilation tube 44 usually remains in place for three to nine months during which time the Eustachian tube 26 blockage subsides. When the tube 44 dislodges, the eardrum 22 heals; the Eustachian tube 26 then resumes its normal pressure equalizing function.

Another method of relieving the pressure in the middle ear 14 is shown in FIG. 4 in which a hypodermic needle 46 is driven through the eardrum 22 through which any accumulated fluid can be withdrawn from typically only the upper portion of the Eustachian tube 26.

The methods of FIGS. 3 and 4 involve rupturing the eardrum 22 to relieve the fluid accumulation and pressure increase in the middle ear. Neither of these methods, in addition to the sometimes permanent puncture created in the eardrum 22, is especially effective in removing all of the fluid in the Eustachian tube 26 since often the lower end 28 thereof is blocked and dammed with fluid.

In connection with the above surgical treatments of FIGS. 3 and 4, Eustachian tube 26 inflation is also employed to relieve the pressure build-up and fluid accumulation as shown in FIG. 5. The hypodermic syringe 46 (shown with a flexible tip 48) is inserted into a nostril or into the mouth until the tip 48 is positioned adjacent the distal opening 28 of the Eustachian tube 26 in the nasopharynx region 30 of the throat 32. Air is blown through the tip 48 via the syringe 46 into the obstructed Eustachian tube 26 and, thus, into the middle ear 14 to help relieve the congestion and reestablish middle ear ventilation. This procedure is often referred to as politzerization. Politzerization is most effective when one of the nostrils is pinched shut (as shown in FIG. 6), while the patient simultaneously swallows. This forces air into the Eustachian tube 26 and the middle ear 14. This technique is good for opening the Eustachian tube 26 but it does not clear accumulated fluid away.

Another method for clearing the middle ear 14 (at least temporarily) is referred to as the "valsalva" maneuver accomplished by forcibly blowing air into the middle ear 14 while holding the nose, often called popping the ear. This method is also good for opening the Eustachian tube 26 but it does not clear the accumulated fluid away either.

Typical disorders associated with the middle ear and the Eustachian tube include perforated ear drums, tympanosclerosis, incus erosion, otitis media, cholesteotoma, mastoiditis, patulous Eustachian tube, and conductive hearing loss. To treat some of these disorders, ear surgery may be performed. Most ear surgery is microsurgery, performed with an operating microscope. Types of ear surgery include stapedectomy, tympanoplasty, myringotomy and ear tube surgery.

One of the simplest ear surgeries is the myringotomy or the incision of the ear drum. However, ear surgery can also require the removal of the tympanic membrane for the visualization of the middle ear space. Often surgeons will try to preserve the integrity of the membrane by making incisions in the skin of the ear canal and removing the tympanic membrane as a complete unit. Alternatively, middle ear access is achieved via the mastoids. This method approaches the middle ear space from behind the ears and drills through the mastoid air cells to the middle ear. Whether the bony partition between the external ear canal and the mastoid is removed or not depends on the extent of the disease. Canal-wall-down refers to the removal of this bony partition. Canal-wall-up refers to keeping this bony partition intact. The term modified radical mastoidectomy refers to an operation where this bony partition is removed and the eardrum and ossicles are reconstructed. A radical mastoidectomy is an operation where this bony partition is removed and the ear drum, malleus and incus bones are permanently removed so that the inner lining of the large cholesteatoma sac can be safely cleaned. This operation is done when an extensive cholesteatoma is encountered or one that is adherent to the inner ear or facial nerve.

Afflictions of the middle ear and Eustachian tubes are very prevalent and a serious medical problem, afflicting millions of people and causing pain, discomfort and even hearing loss or permanent ear damage. Although a number of treatments have been developed, as described above each of them has shortcomings. Therefore, a need exists for improved methods and systems for accessing, diagnosing and treating target tissue regions within the middle ear and the Eustachian tube. Ideally, such methods and systems would be minimally invasive and pose very little risk of damage to healthy ear tissue.

BRIEF SUMMARY OF THE INVENTION

The embodiments of the present invention are directed toward methods and systems for accessing, diagnosing and/or treating target tissue regions within the middle ear and the Eustachian tube. The healthy Eustachian tube opens naturally when adjacent muscles contract to vent the middle ear and provide a gas pathway. Devices may be implanted within or along the Eustachian tube to help intermittently open the Eustachian tube. One type of device utilizes a valve tethered or otherwise operatively coupled to muscles adjacent to the Eustachian tube, and particularly to muscles responsible for opening the Eustachian tube. Such devices may ameliorate disorders which prevent the Eustachian tube from opening, including those caused by thickening of mucosal wall tissue or the like. In some embodiments, when the muscles contract the tethers will move and cause the valve to open and vent the middle ear. Another type of device utilizes compressive tethers on a portion of the mucosa and adjacent cartilage, to compress and shrink the mucosa and help the Eustachian tube open. Another device comprises an elongated spring, which can be implanted within or along the Eustachian tube to aid in opening of the Eustachian tube.

In one embodiment of the invention, a method for providing a gas pathway in the middle ear region of a patient is provided. A guide wire is advanced into the Eustachian tube (ET) of the patient via the patient's nasopharynx. An endoluminal ET ventilating implant is introduced via the patient's nasopharynx along the guide wire into the Eustachian tube of the patient. The implant is advanced into the ET adjacent the cartilage and tensor villi palatine or the levator villi palatine muscles. The implant is dimensioned for insertion into the ET adjacent the nasopharynx. The implant is tethered to the ET cartilage using a first connector. The implant is tethered to the tensor villi palatine or the levator villi palatine muscles using a second connector. A gas pathway is provided between the ET lumen and the nasopharynx using the implant, the implant being dimensioned and configured to modulate an opening in a gas pathway in communication with the ET lumen and the nasopharynx.

In many embodiments, the implant comprises a tube located in the ET lumen. In many embodiments, the implant further comprises a valve in fluid communication with the lumen, the valve having a first valve portion and a second valve portion, the first valve portion being connected with said first connector, and said second valve portion being connected with said second connector. The valve can be configured to modulate the opening during swallowing due to movement of the tensor villi palatine or the levator villi palatine muscles.

In many embodiments, the guide wire includes at least one marking and the method further comprises viewing a location of the marking relative to anatomy of the patient during the advancing method to determine how far to advance the guide wire into the ET.

In another embodiment of the invention, an endoluminal implant for providing a gas pathway between the nasopharynx and the Eustachian tube (ET) is provided. The implant comprises a lumen dimensioned for insertion into the ET at an end adjacent the nasopharynx, through the patient's nasopharynx. A valve is in fluid communication with the lumen. The valve has a first valve portion and a second valve portion. A first connector portion is connected with the first valve portion to tether the implant to the cartilage adjacent the ET. A second connector portion is connected with the second valve portion to tether the implant to the adjacent tensor villi palatine or the levator villi palatine muscles.

In many embodiments, the first connector portion comprises a first tether configured to span across the cartilage and compress the mucosa of the ET lumen to secure the first valve portion with the cartilage. The proximal end of said first connector portion can have a T-shaped member to secure against the cartilage.

In many embodiments, the valve is configured to modulate opening of the ET during swallowing. The valve can be configured to modulate opening of the ET in response to the movement of the tensor muscles.

In yet another embodiment of the invention, another method for providing a gas pathway in the middle ear region of a patient is provided. An endoluminal ET ventilating implant is introduced via the patient's nasopharynx into a Eustachian tube (ET) of a patient. A gas pathway is provided between the ET lumen and the nasopharynx using the implant. The implant is dimensioned and configured to modulate an opening in a gas pathway in communication with the ET lumen and the nasopharynx. In many embodiments, the implant comprises an elongated spring member which applies a constant force against the ET.

In yet another embodiment of the invention, another endoluminal implant for providing a gas pathway between the nasopharynx and the Eustachian tube (ET) is provided. The implant comprises an elongated spring member dimensioned for insertion into the ET at an end adjacent the nasopharynx, through the patient's nasopharynx. The elongated spring member applies a force to modulate an opening in a gas pathway in communication with the ET lumen and the nasopharynx. In many embodiments, the implant is configured to cause tissue ingrowth.

In yet another embodiment of the invention, another method for providing a gas pathway in the middle ear region of a patient is provided. An implant is introduced via the patient's nasopharynx into a Eustachian tube (ET) of a patient. The implant is coupled to adjacent cartilage to compress a wall of the ET. A gas pathway is provided between the ET lumen and the nasopharynx using the tethering implant.

In yet another embodiment of the invention, another endoluminal implant for providing a gas pathway between the nasopharynx and the Eustachian tube (ET) is provided. The implant comprises a first connector portion, and a member with a first end and a second end. The first end is connected to the first connector portion. A second connector portion is configured to attach to the second end of the member. The member is of a suitable length, so that the member compresses a portion of the ET wall between the first and second ends.

For a further understanding of the nature and advantages of the invention, reference should be made to the following description taken in conjunction with the accompanying figures. Each of the figures is provided for the purpose of illustration and description only and is not intended to limit the scope of the embodiments of the present invention.

BRIEF DESCRIPTION OF THE DRAWINGS

FIGS. 13A and 13B show perspective and side views, respectively, of a device for treating a disorder of a Eustachian tube, according to one aspect of the invention.

FIG. 13C shows a perspective view of a portion of a treated Eustachian tube, according to one aspect of the invention.

DETAILED DESCRIPTION OF THE INVENTION

The embodiments of the present invention are directed toward methods and systems for accessing, diagnosing and treating target tissue regions within the middle ear and the Eustachian tube.

Access

Figure 1:
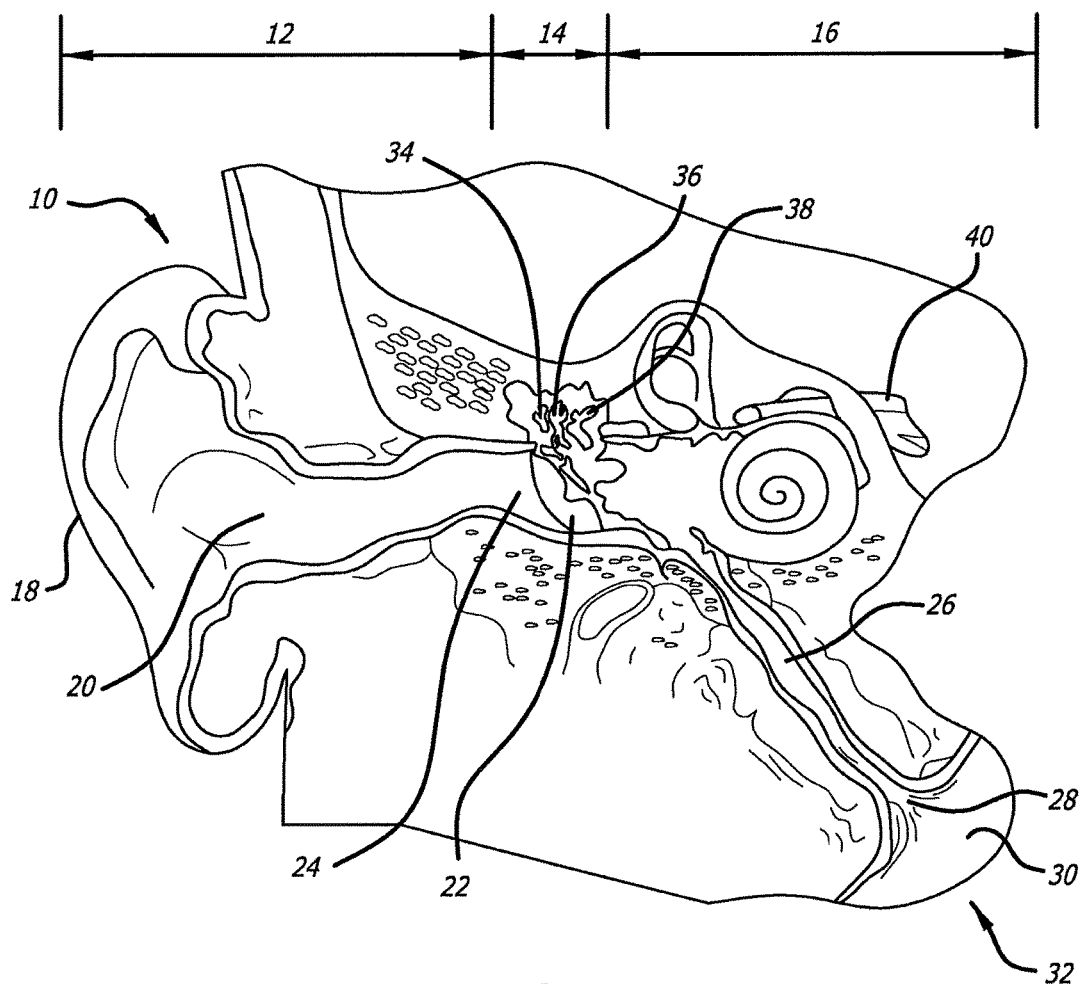
FIG. 1 is a cross section of a human ear showing the inner, middle and outer ear portions and the Eustachian tube connecting the middle ear with the nasopharynx region of the throat via a distal opening thereof.
Figure 2:
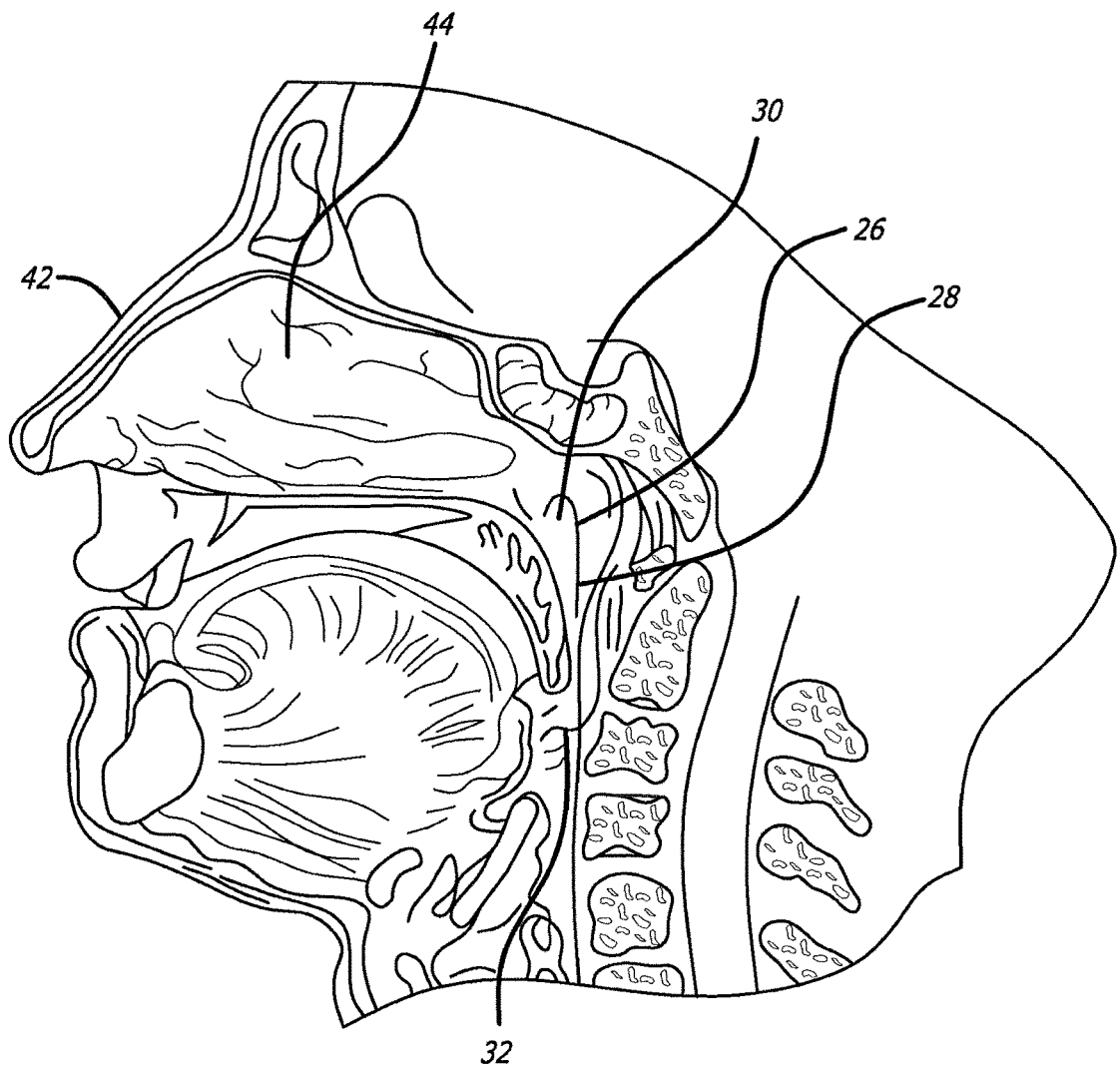
FIG. 2 is a cross section of a human head showing the nasopharynx region of the throat illustrated in FIG. 1 containing the distal opening of the Eustachian tube illustrated in FIG. 1.
Figure 3:
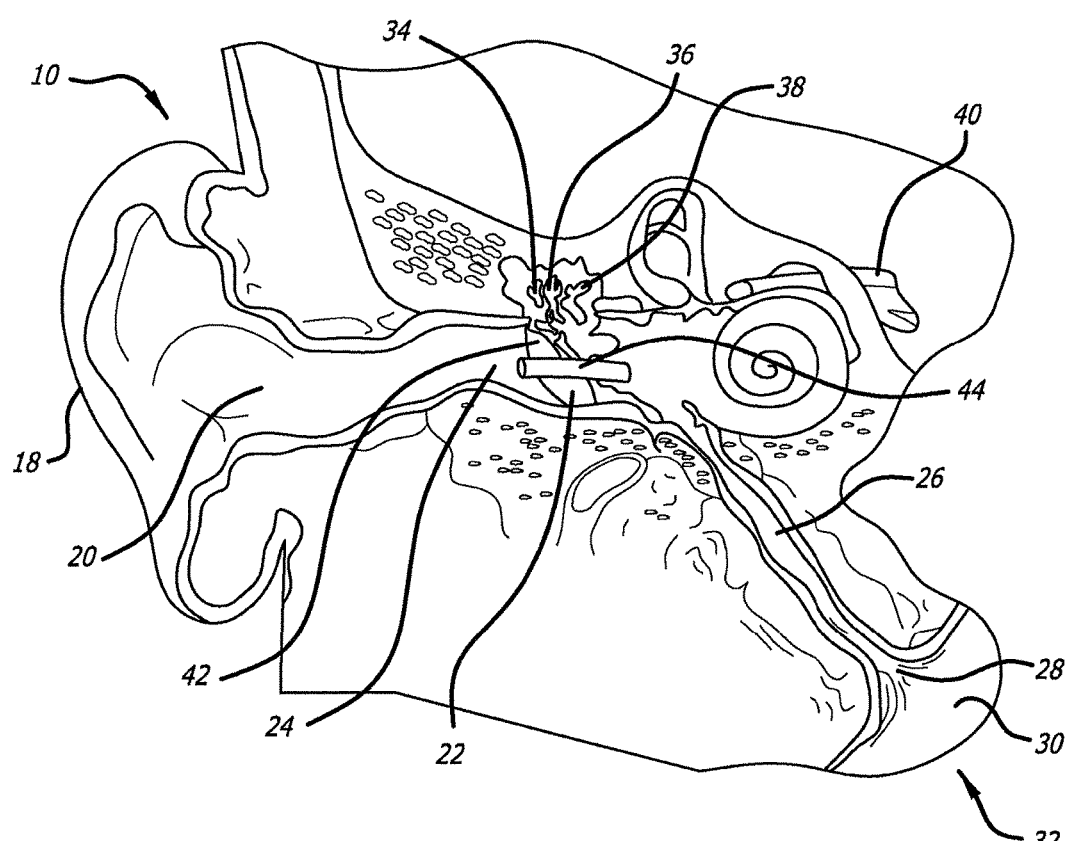
FIG. 3 is a cross section of a human ear in the orientation shown in FIG. 1 showing a prior art surgical method for relieving fluid in the middle ear in which a ventilation tube is placed within an incision in the eardrum.
Figure 4:
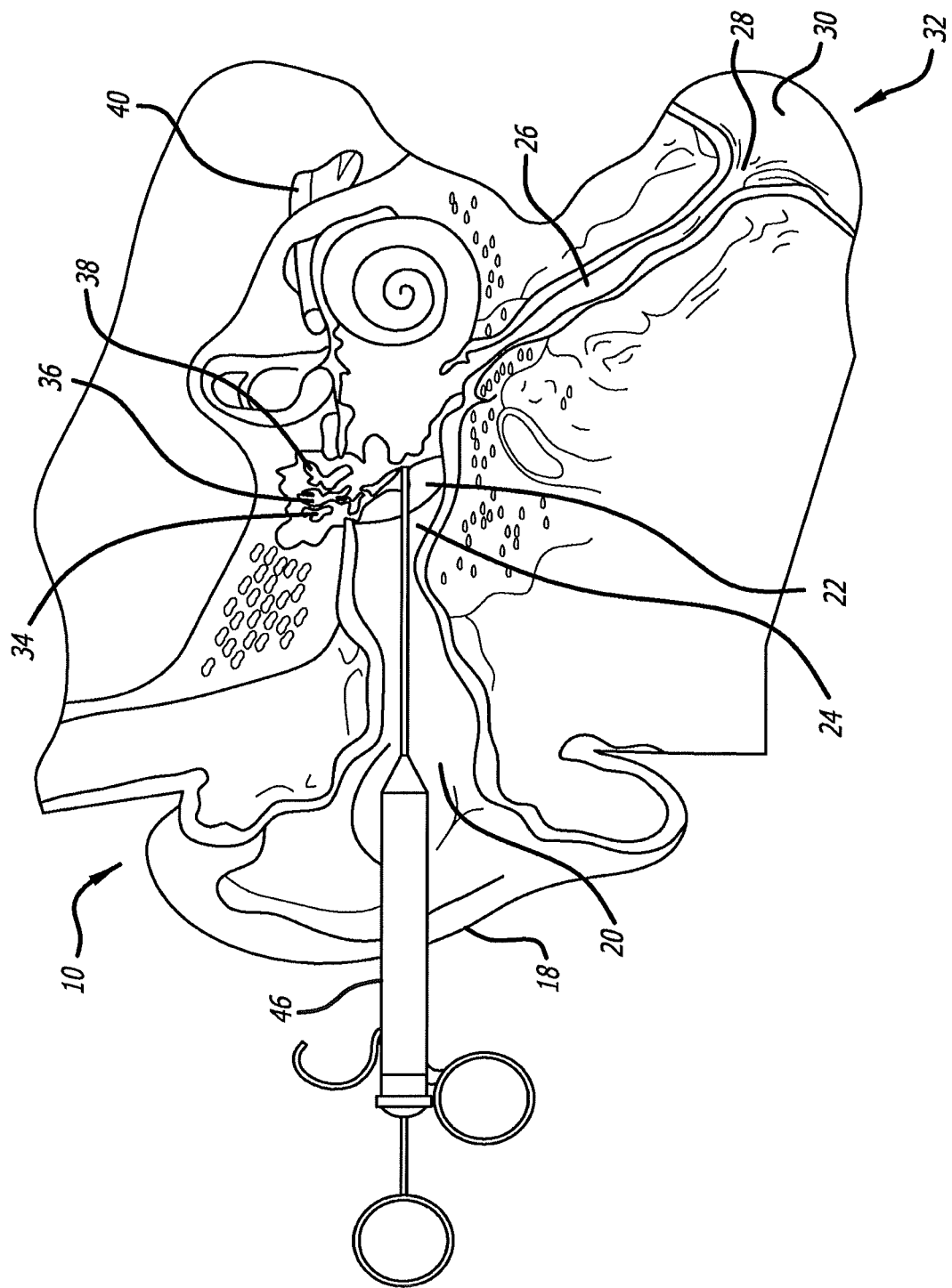
FIG. 4 is a cross section of a human ear in the orientation shown in FIG. 1 showing a prior art surgical method for relieving fluid in the middle ear in which a syringe is shown having a needle perforating the eardrum.
Figure 5:
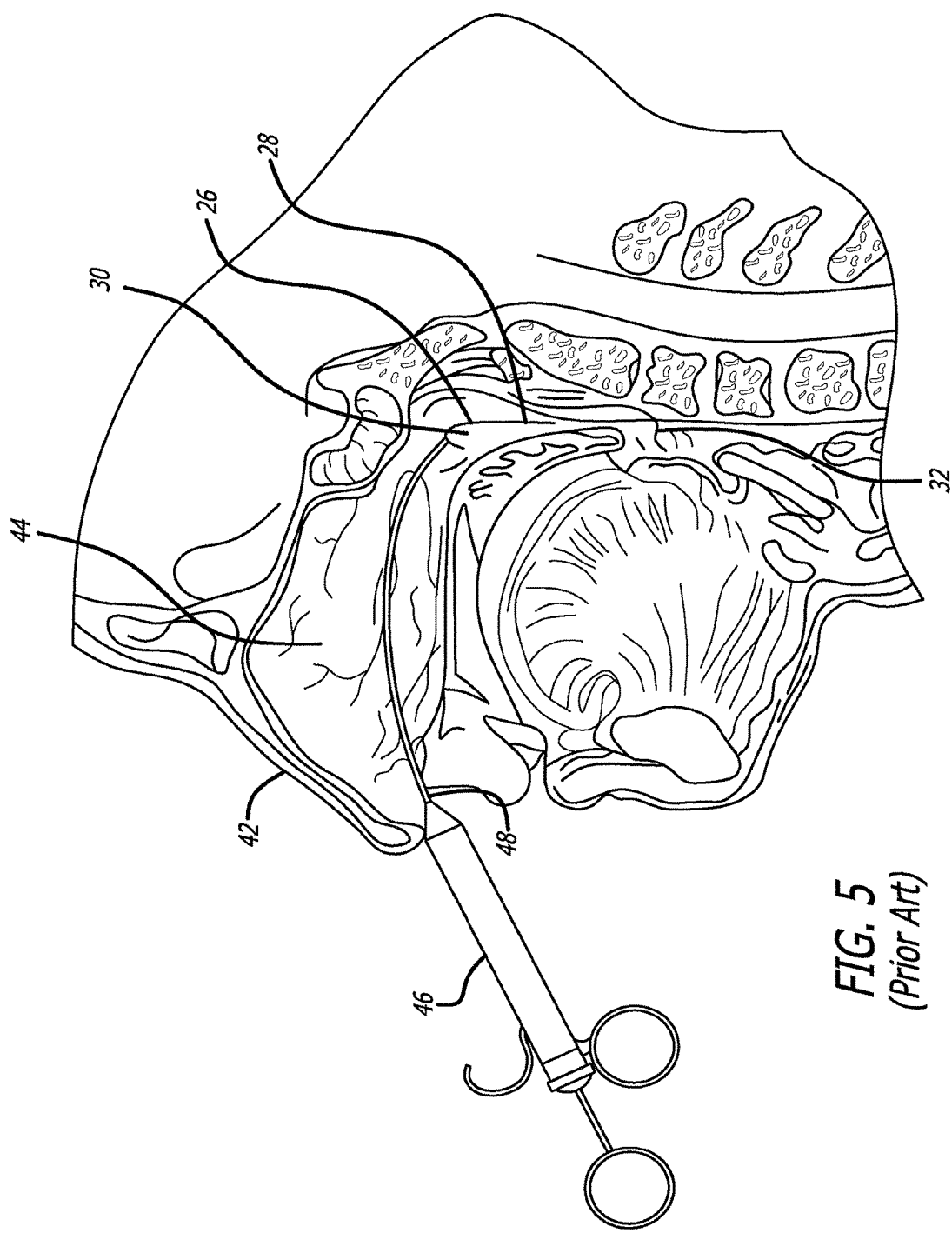
FIGS. 5-6 show a cross section of a human head in the orientation shown in FIG. 2 showing a prior art politzeration method for relieving fluid in the middle ear in which a syringe is shown having a flexible tip extending into the nose and/or throat area so that the tip abuts the distal opening of the Eustachian tube while the nose is plugged.
Figure 6:
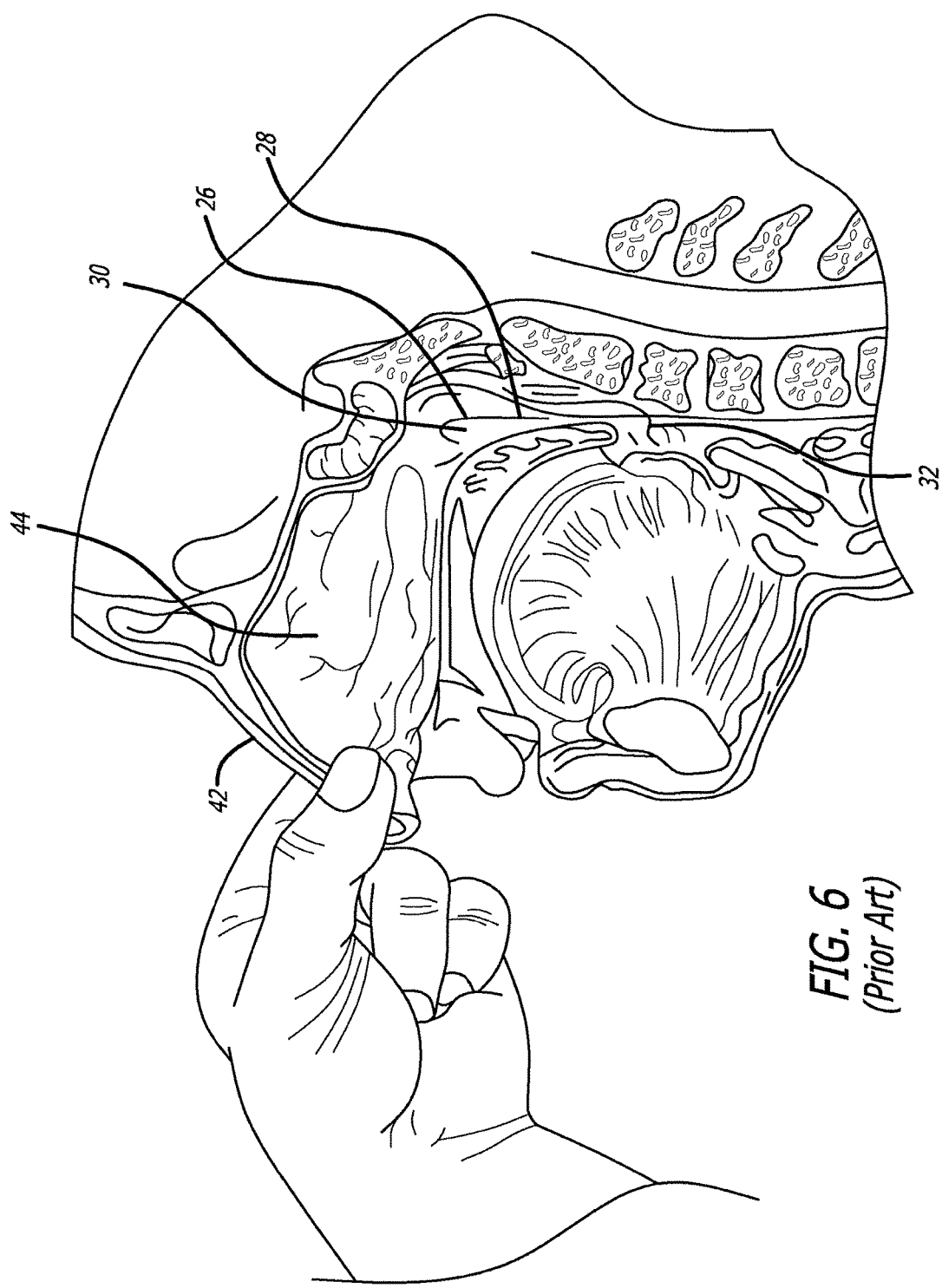
Figure 7:
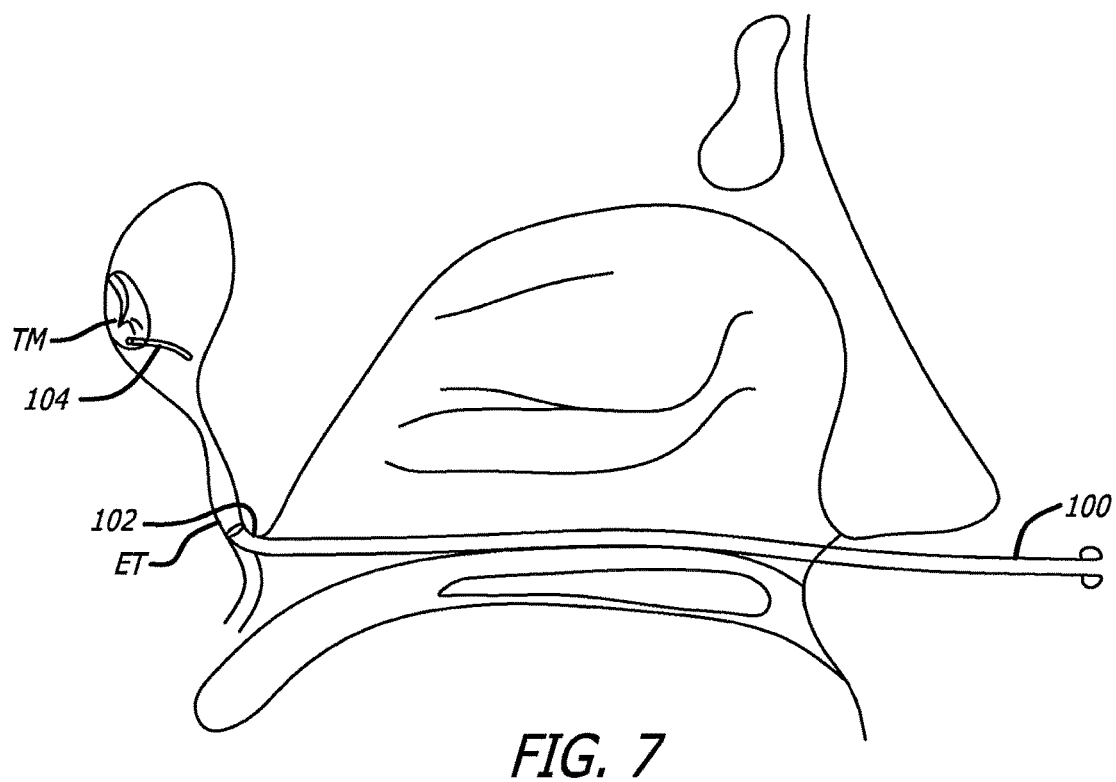
FIG. 7 shows a cross sectional view of a human head showing the nasopharynx region and a guide catheter in the nasal passage where the distal tip of the guide catheter is adjacent the Eustachian tube opening.
Figure 8:
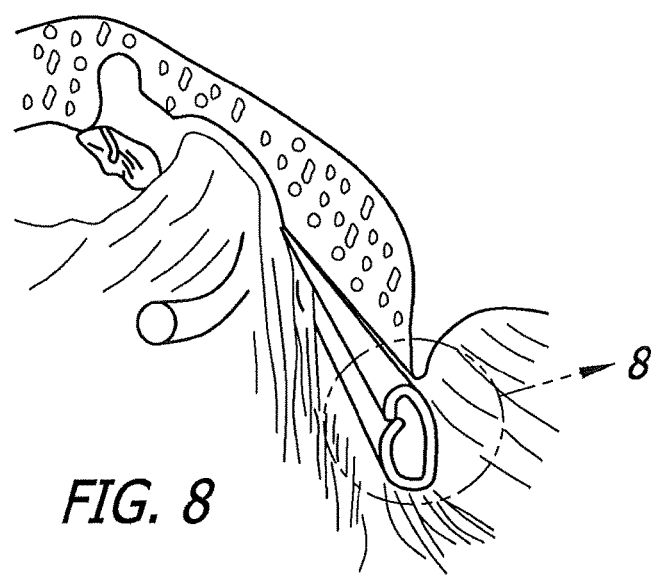
FIG. 8 shows a section of the anatomical region around a Eustachian tube (ET).

One embodiment of the present invention is directed toward using minimally invasive techniques to gain trans-Eustachian tube access to the middle ear. A middle ear space may be accessed via a Eustachian tube (ET). To obtain this access to the Eustachian tube orifice, a guide catheter having a bend on its distal tip greater than about 30 degrees and less than about 90 degrees may be used. Once accessed, diagnostic or interventional devices may be introduced into the Eustachian tube. Optionally, to prevent damage to the delicate middle ear structures, a safety mechanism may be employed. In one embodiment, the safety mechanism may include a probe and/or a sensor introduced into the middle ear via the tympanic membrane as shown in FIG. 7. For example, the probe may be an endoscope, and the sensor may be an electromagnetic transducer.

FIG. 7 is a cross sectional view showing the nasopharynx region and a guide catheter 100 in the nasal passage where the distal tip 102 of the guide catheter is adjacent the Eustachian tube opening. FIG. 7 shows the guide catheter 100 having a bend on its distal tip 102 that is greater than about 30 degrees and less than about 90 degrees located adjacent the Eustachian tube orifice. A sensor 104 located adjacent the tympanic membrane may be used to monitor advancement of the guide catheter. The sensor is one example of a safety mechanism.

Diagnosis

Another embodiment of the present invention is directed to diagnosis of the condition of the middle ear and its structure. In one embodiment, diagnosis may include use of an endoscope that has been advanced into position through the guide catheter 100. The design of the endoscope will allow for a 90 degree or more Y axis visualization and a 360 degree rotation. Such an endoscope may be used for assessment of cholesteotomas, ossicle function and/or condition, and the surgical follow-up. An exemplary endoscope that may be adapted as described above may use the IntroSpicio 115 1.8 mm camera developed by Medigus. Such a camera measures approximately 1.8 mm×1.8 mm and its small rigid portion allows for the maximum flexibility at the endoscope tip.

Alternatively, ultrasound may be used by injecting a fluid into the middle ear space and the ET and scanning the middle ear and the ET and its structure ultrasonically. Post-procedure the fluid may be aspirated or left to drain through the Eustachian tube. An ultrasound tipped catheter may be advanced up the ET to a position at the middle ear cavity. The ultrasound catheter may then be pulled down the ET and the physician may use an external video monitor to view the structure in and adjacent the ET.

Functional diagnosis of the Eustachian tube may be achieved via direct or indirect assessment. In one embodiment, for direct assessment, the diagnostic system may allow for the dynamic monitoring of the Eustachian tube during swallowing via a diagnostic probe inserted via the nasopharynx. Since such a diagnostic system may be used dynamically during swallowing, the probe may be made of a flexible and durable material configured to be atraumatic. In one embodiment, the guide catheter(s) 100 used in the nasopharynx approach may be removed once the diagnostic probe is in or near the ET region and prior to the swallowing.

In one embodiment, the diagnostic probe may comprise an endoscope to visualize the ET structure and function. Alternatively, the diagnostic probe may include a pressure transducer located on a catheter or a wire. When a pressure transducer is used, the pressure within the ET may be monitored during swallowing and the pressure measurements may be interpreted for ET opening function. Alternatively, an ultrasound probe may be inserted in the ET lumen to scan the ET region's structure. Fluid may be introduced into the ET to facilitate ultrasound diagnosis. For any of the above diagnostic systems, a single short length transducer that is repositioned after each swallow may be used. Alternatively, an array of transducers may be used to facilitate mapping of all or a portion of an ET.

The techniques described above may be used to directly access and diagnose a Eustachian tube of a patient. In one embodiment, a method for accessing a Eustachian tube of a patient may include inserting a guide catheter into a nasal passage of the patient, the guide catheter having a distal tip with a bend having an angle between about 30 and about 90 degrees; and advancing the guide catheter in the nasal passage toward an opening of the Eustachian tube in the nasopharynx to place the distal tip adjacent the Eustachian tube opening. Additionally, the method may also include advancing a diagnostic device through the guide catheter to place a distal tip of the diagnostic device adjacent the Eustachian tube opening. The diagnostic device may include a diagnostic catheter. The diagnostic device may include an endoscope, a pressure transducer, or an ultrasound catheter.

Additionally, the method may also include introducing a diagnostic probe into the Eustachian tube to directly assess Eustachian tube function. It is preferred that the diagnostic probe is made from a flexible and Eustachian tube compatible material. Alternatively, the diagnostic probe may comprise a pressure transducer located on a guide wire, and whereby the method also includes monitoring pressure within the Eustachian tube while the patient is swallowing; and assessing an opening function of the patient's Eustachian tube using the monitoring. The method may also include removing the guide catheter after the diagnostic probe is placed into the Eustachian tube. Additionally, or alternatively, the diagnostic probe may comprise an ultrasound probe.

For indirect functional diagnosis of a Eustachian tube, in some embodiments, an external energy source may be used to assess opening of the Eustachian tube. For example, possible energy sources may include, but are not limited to, pressure, sound, light or other electromagnetic energy. In one embodiment of indirect assessment, an emitter may be positioned in the nasopharynx and a receiver may be placed at the tympanic membrane. Correlation between the emitted signal and the received signal may be translated into the physical characteristics of the ET during swallowing.

The techniques described above may be used to implement procedures for indirectly accessing and diagnosing the Eustachian tube of a patient. The indirect assessment method includes positioning an energy emitter in the nasopharynx adjacent a Eustachian tube, positioning an energy receiver adjacent the tympanic membrane via the external ear canal; directing energy from the emitter toward the receiver; generating an emitter signal representative of the energy from the emitter; generating a receiver signal representative of the energy received by the emitter; forming a comparison between the emitter signal and the receiver signal; and indirectly assessing function of the Eustachian tube during swallowing, using the comparison. The energy emitter can be a device that emits energy in the form of a pressure wave or electromagnetic energy. The indirect assessment may also include estimating the physical characteristics of Eustachian tube.

Treatment

An embodiment of the present invention is directed toward the treatment of Eustachian tube disorders. In some cases, for example, Eustachian tube disorders may be related to the Eustachian tube being unable to open or close. In some cases mucosal tissue of the Eustachian tube may thicken, such that the adjacent muscles become ineffective in opening the Eustachian tube in order to provide a gas pathway between the Eustachian tube and the nasopharynx.

Figure 9A:
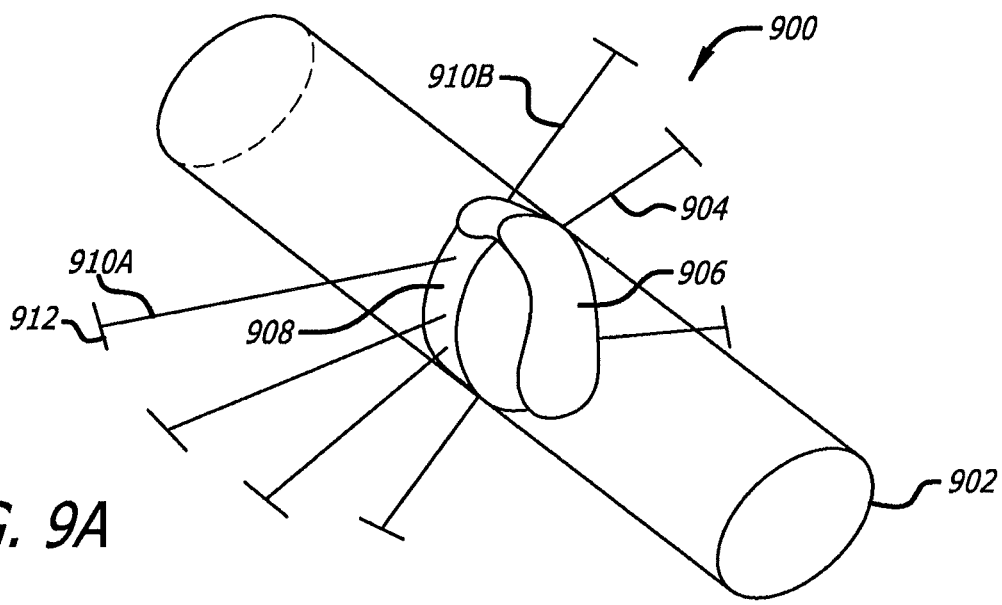
FIG. 9A shows a perspective view of a device for treating a disorder of a Eustachian tube, according to one aspect of the invention.

FIG. 9A shows a perspective view of a device 900 for supporting a Eustachian tube, according to another embodiment of the invention. The device 900 includes a lumen 902 which is in fluid communication with a valve 904. The lumen 902 is configured to be inserted into the Eustachian tube, and accordingly includes a suitable length and diameter, for example, approximately 35 mm and 1.5 mm respectively. Although the lumen 902 is shown with a circular profile, the lumen 902 may be of other suitable shapes, such as a crescent, for matching the transverse profile of the Eustachian tube. The lumen 902 can be made from a variety of materials, for example, biocompatible metals and polymers. The lumen 902 can be constructed in a variety of ways, for example, expandable mesh (stent), woven graft, or pre-formed (molded). In some embodiments, the lumen 902 can include therapeutic substances which elute over time in order to provide a desired tissue response, for example, causing tissue to grow into exterior portions of the lumen, and/or preventing tissue from growing excessively into the interior of the lumen.

The valve 904 is shown to include a first valve portion 906 and a second valve portion 908. The valve 904 is normally in a closed configuration when implanted, with the first and second valve portions sealingly engaging each other, as the Eustachian tube is also normally closed. The first and second valve portions are configured to open and close with physiological movement of tissues near the Eustachian tube, typically with movement of the tensor villi palatine or the levator villi palatine muscles (depending on which ear the device 900 is placed in), for example, during swallowing. The first and second valve portions can include tethers 910 or other tension members. The members or tethers can (but need not) comprise laterally flexible tension members. One side of the tethers 910A can be connected to the tensor villi palatine or the levator villi palatine muscles. Another side of the tethers 910B can be connected to cartilage adjacent to the Eustachian tube. Accordingly, movement of the tensor villi palatine or the levator villi palatine muscles will cause the tethers 910A to move and in turn cause the second valve portion 908 to separate from the first valve portion 906, and cause the Eustachian tube to open.

The tethers 910A are intended to be able to move with the tensor villi palatine or the levator villi palatine muscles, and are configured to pass through the Eustachian tube wall. The tethers 910A may incorporate outer sleeves (not shown) for tissue to adhere to, but still allow movement of the tethers 910. The tethers 910B are intended to pass through the Eustachian tube wall and connect to adjacent cartilage. The tethers 910B are not required to move. The tethers 910B can be of appropriate length to compress surrounding mucosa and thus reduce the effective inner diameter of the Eustachian tube. The tethers 910 are connected to the appropriate muscles or cartilage through anchoring members 912 which anchor to tissue. The valve 903 is shown to occupy a portion of the lumen 902, however, in some embodiments the valve may occupy the entirety of the lumen when in the closed configuration. In some embodiments, a plurality of valves 904 may occupy the lumen 902.

Figure 9B:
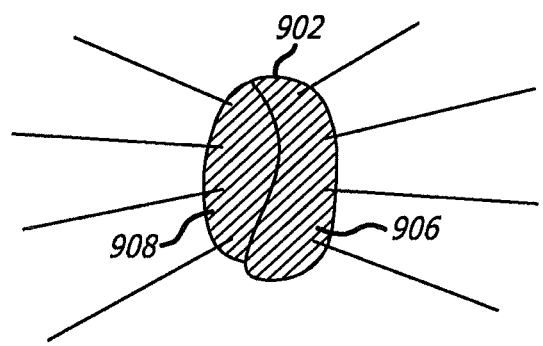
FIGS. 9B and 9C show cross-sectional views of the device of FIG. 9A.
Figure 9C:
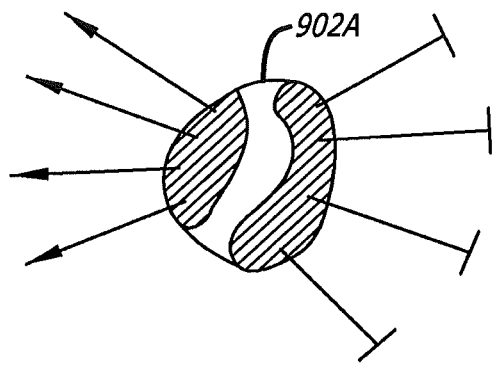

FIGS. 9B and 9C shows a cross-sectional views of the device 900. The device includes a closed position as shown in FIG. 9B. The valve 904 is closed when the tensor villi palatine or the levator villi palatine muscles are not contracted, and not pulling on tethers 910A. The valve 904 is open when the tensor villi palatine or the levator villi palatine muscles contract or shorten, and pull on tethers 910A to move the second valve portion, as shown in FIG. 9C. A portion 902A of the lumen 902 may be stretchable or foldable, such that when the valve 902 opens a pathway is present between the first and second valve portions when the valve 902 is open. Accordingly, the lumen 902 may comprise a stretchable and/or flexible material, such as silicone.

Figure 10A:
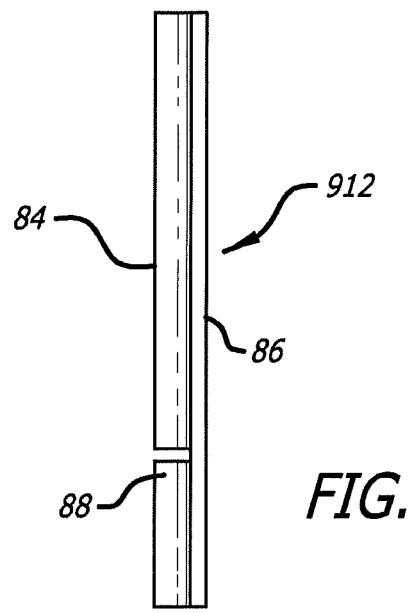
FIGS. 10A and 10B show perspective views of an anchoring member 912, according to one aspect of the invention.
Figure 10B:
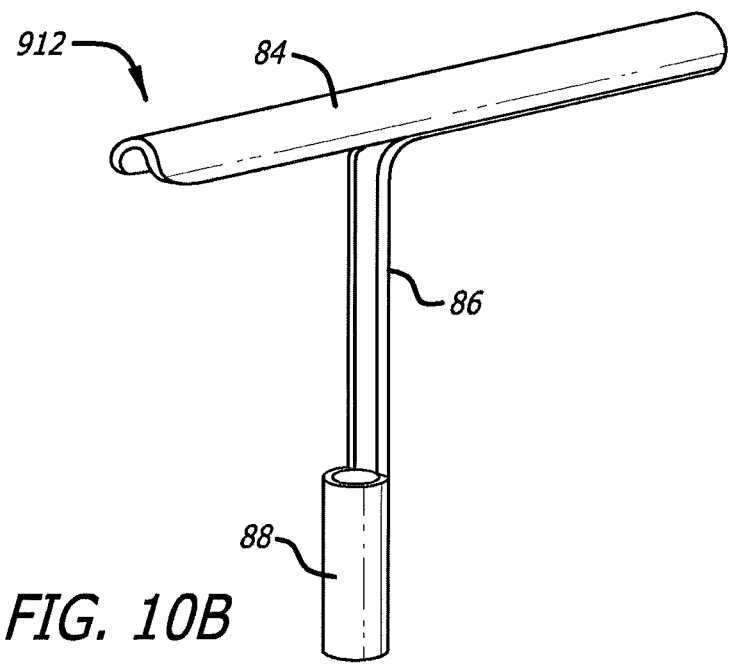

FIGS. 10A and 10B shows perspective views of an anchoring member 912 according to one embodiment of the invention. In an unconstrained configuration, the first component forms a generally T-configuration (FIG. 10B). When constrained within an anchor delivery device, the first component defines a substantially straight member (FIG. 10A). While the component can be formed from a number of materials and manufactured using various conventional approaches. The anchoring member 912 can be cut from a Nitinol™ tube using a laser. Using a superelastic material such as Nitinol™ provides the component 82 with the resiliency to transform between a flipped T-configuration and a straight configuration.

As shown, the anchoring member 912 includes a first portion 84 which at one end defines a cylindrical structure and at the other a partial cylindrical structure. When unconstrained, this first portion 84 forms a T-bar or top of the anchoring member 82. A complementary partial cylindrical structure forms a mid-section or second portion 86 of the anchoring member 82 and operates as a spring to accomplish the flipping of the first portion 84 between constrained and unconstrained configurations. When the component is in its constrained, straight form, the second portion is positioned adjacent the first portion 84. A third portion 88 is also cylindrical in shape and extends from the second portion 86 away from the first portion 84. The third portion 88 can attach to one end of a tether 910. Another anchoring member can attach to the other end of the tether. One commonly skilled in the art would recognize that other types of anchoring devices may be used or adapted, and devices for implanting such anchoring devices, for example, as shown and described in U.S. patent application Ser. No. 11/492,690, Publication No. 2007/0049929A1 (now U.S. Pat. No. 7,896, 891), the entirety of which is incorporated herein in its entirety.

Figure 11A:
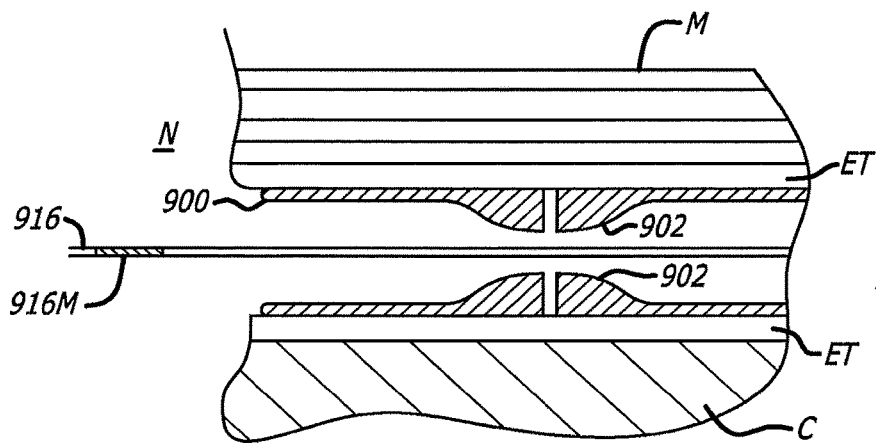
FIGS. 11A-11C show cross-sectional views of a device being positioned within or along a Eustachian tube, according to one aspect of the invention.

FIG. 11A shows a partial cross-section of an Eustachian tube ET, including surrounding tensor villi palatine or the levator villi palatine muscles M, and adjacent cartilage C. The device 900 has been placed using a guide wire 916. The guide wire 916 is inserted via a patient's nasopharynx. A suitable nasal endoscope may be used to place the guide wire. The guide wire 916 can include a marker 916M to which can be aligned with a feature of the Eustachian tube, such as the entry way, to determine how far to advance the guide wire into the Eustachian tube. The device 900 is shown placed in the Eustachian tube ET. The device 900 is shown in an expanded state for the sake of clarity, but may be collapsed around the guide wire in actual use.

Figure 11B:
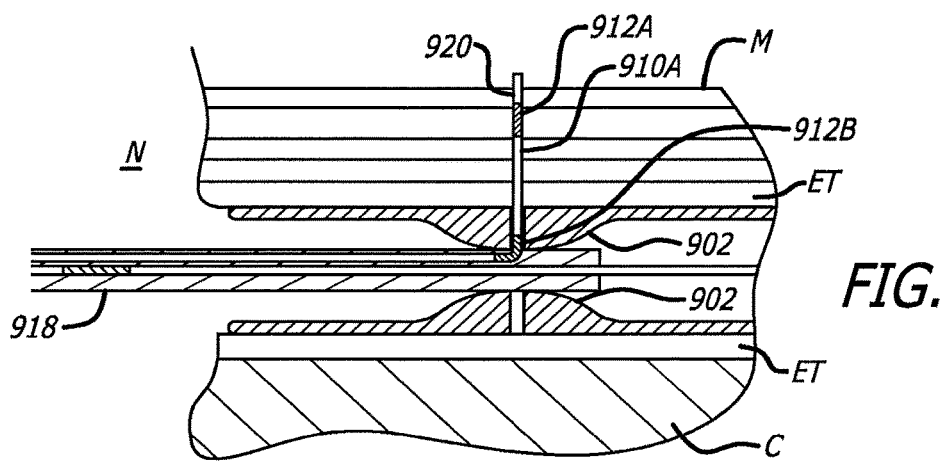

FIG. 11B shows a partial cross-section of the Eustachian tube ET of FIG. 11A. A catheter 918 is advanced over the guide wire 916 and placed partially within the device 900. The catheter 918 includes a hollow needle 920 which is advanced through an opening within the device 900 about valve 902 and through the Eustachian tube ET and tensor villi palatine or the levator villi palatine muscles M. A tether 910A and two connected anchoring members 912A, 912B reside within the needle. Anchoring member 912A can be ejected from the needle 920 within or along the tensor villi palatine or the levator villi palatine muscles M. The anchoring member 912A can then form a T-shape as discussed herein, and anchor itself within or along the tensor villi palatine or the levator villi palatine muscles M. The needle 920 may then be withdrawn to a position about the device 900 and anchoring member 912B may be ejected from the needle 920. The anchoring member 912A can then form a T-shape, and anchor itself to the device 900. The tether 910A connects the anchoring members 912A, 912B. At least one tether may also be placed into the cartilage C using the same method.

Figure 11C:
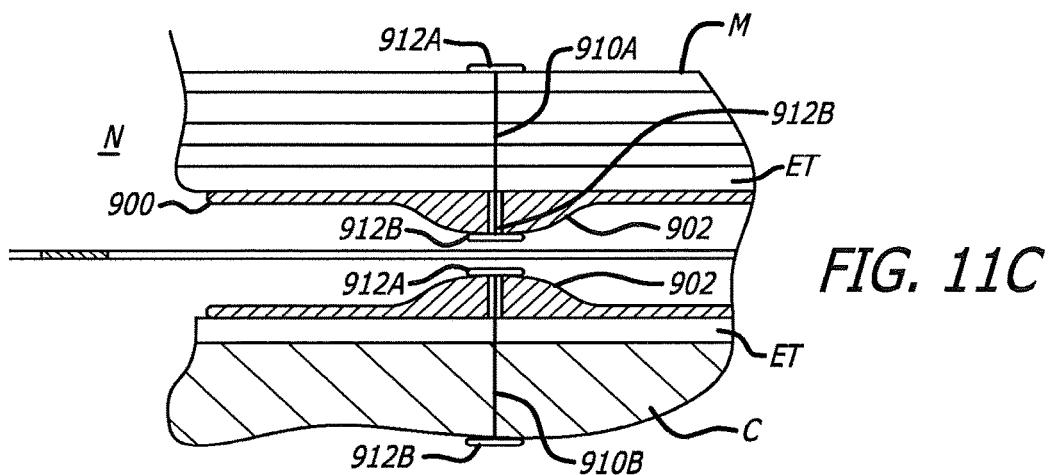

FIG. 11C shows a partial cross-section of the Eustachian tube ET of FIG. 11A. The device 900 is shown connected about valve 902 to the tensor villi palatine or the levator villi palatine muscles M by at least one tether 910A. The device 900 is also shown connected about valve 902 to the cartilage C by a tether 910B. Shortening or contraction of the tensor villi palatine or the levator villi palatine muscles M can open the valve 902, for example, during swallowing. Thus, the device can provide a gas pathway between the ET lumen and the nasopharynx.

Figure 11D:
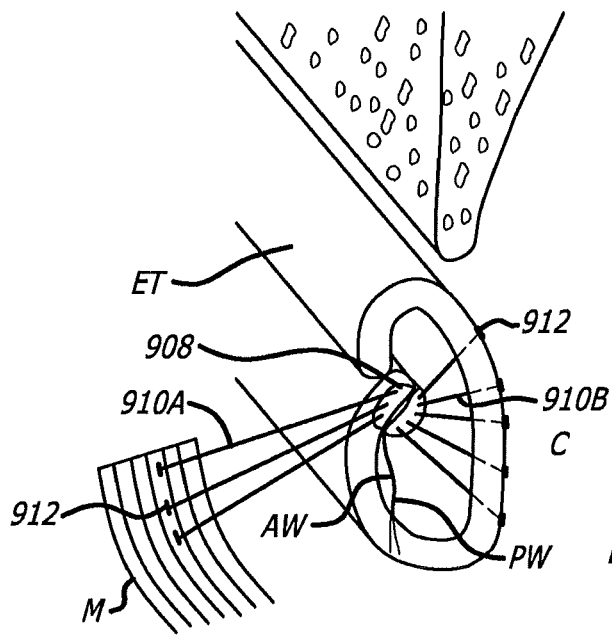
FIG. 11D shows a perspective view of a portion of a treated Eustachian tube, according to one aspect of the invention.

FIG. 11D shows a perspective view of the device 900 implanted within or along to a Eustachian tube. Multiple tethers 910A connect the second valve portion 908 to the tensor villi palatine or the levator villi palatine muscles M. Similarly, multiple tethers 910B connect the first valve portion 906 to the cartilage C. The device 900 is shown in a closed position with the first and second valve portions in contact with each other. The Eustachian tube is normally closed with the posterior and anterior walls of the Eustachian tube in contact. The Eustachian tube opens to relieve pressure or fluids upon contraction of the tensor villi palatine or the levator villi palatine muscles M, and thus separate the anterior wall AW from the posterior wall PW.

Figure 12:
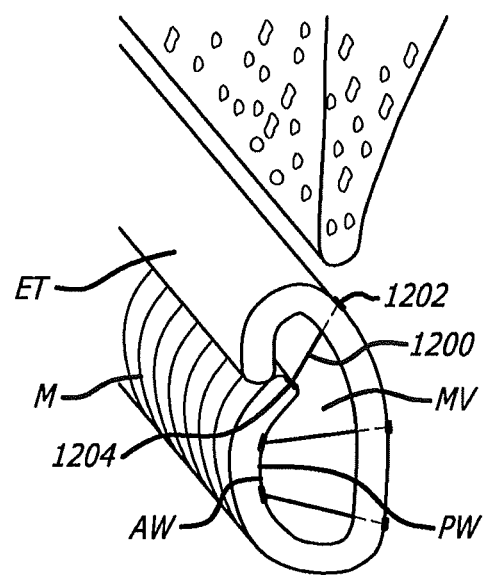
FIG. 12 shows a perspective view of a portion of a treated Eustachian tube, according to one aspect of the invention.

FIG. 12 shows a perspective view of a portion of a Eustachian tube ET. As noted above, Eustachian tube disorders can originate from a thickening of the mucosa MU on the posterior wall of the Eustachian tube. When the mucosa MU becomes too thick, contraction of the tensor villi palatine or the levator villi palatine muscles M can be ineffective to open the Eustachian tube. Tethers 1200 are shown at least partially implanted within or along the mucosa MU with anchors 1202, 1204 positioned within or along the cartilage C and mucosa MU. The tethers 1200 and anchors 1202, 1204 can be implanted as similarly discussed herein. The tethers 1200 can be of an appropriate length, for example as long as the transverse thickness of a normal mucosa, which may be patient dependent, in order to compress and shrink the thickened mucosa MU to a normal thickness. Accordingly, contraction of the tensor villi palatine or the levator villi palatine muscles M can then be effective in separating the anterior wall AW from the posterior wall PW of the compressed Eustachian tube. A plurality of tethers can be placed throughout the Eustachian tube. In some embodiments, the tethers or anchors are attached to support members (not shown) placed within or along the Eustachian tube, for supporting the tissue of the Eustachian tube and/or to provide a valve.

FIGS. 13A and 13B show perspective and end views, respectively, of a spring member 1300 for supporting a Eustachian tube. The spring member 1300 can be configured in an elongated clamshell configuration as shown. A first portion 1302 of the spring member 1300 is configured to be positioned along and/or a the posterior wall of the Eustachian tube. A second portion 1304 of the spring member 1300 is configured to be positioned along and/or about the posterior wall of the Eustachian tube. The first portion 1302 and the second portion 1304 can be spring biased away from each other according to a spring force F to resist the first portion 1302 and the second portion 1304 from coming into contact with one another, with the spring force optionally being substantially constant. The spring member 1300 can comprise a variety of metals and polymers. In some embodiments, the spring member 1300 can be constructed from a plurality of biased wires (shaped in the profile of FIG. 13B) connected by a membrane of material. In some embodiments, the spring member 1300 can be constructed from a single piece of flat material. In some embodiments, the spring member 1300 can be constructed from mesh of interwoven material. In some embodiments, the spring member 1300 can be coated or imbedded with a therapeutic substance, for example, to encourage tissue growth, limit stenosis of the Eustachian tube, and/or the like.

FIG. 13C shows a perspective view of a portion of a Eustachian tube ET. The spring member 1300 is shown implanted sub-mucosally along the Eustachian tube ET. The first portion 1302 and the second portion 1304 of the spring member 1300 are shown implanted along the Eustachian tube, with the first portion 1302 located behind the posterior wall PW, and the second portion located behind the anterior wall AW. The spring member 1300 serves to aid opening of the Eustachian tube as the spring force F helps separate the anterior wall AW from the posterior wall PW, and thus serve as an aid to the tensor villi palatine or the levator villi palatine muscles M. In some embodiments, the spring member 1300 may be surgically implanted behind the anterior wall AW and posterior wall PW, for example by an incision. In some embodiments, the spring member 1300 may include a substance which causes a tissue response to grow into or over the spring member 1300. In some embodiments, the spring member 1300 may be permanently or temporarily positioned on the exterior of the anterior and posterior walls. In some embodiments, the spring member 1300 is biased toward a closed configuration to keep the Eustachian tube closed in the case of a patulous Eustachian tube.

The present invention may be embodied in other specific forms without departing from the essential characteristics thereof. For example, devices and methods for accessing the Eustachian tube as disclosed in co-assigned U.S. patent application Ser. No. 12/340,226 (published as U.S. Pat. Pub. No. 2009/0163890), the entirety of which is incorporated by reference herein, may be used in conjunction with the instant disclosure. These other embodiments are intended to be included within the scope of the present invention, which is set forth in the following claims.

What is claimed is:

1. A method for providing a gas pathway and introducing a therapeutic substance in the middle ear region of a patient, comprising:
    (a) introducing an endoluminal implant via the patient's nasopharynx into a Eustachian tube (ET) of the patient, wherein the endoluminal implant:
        i. contains the therapeutic substance; and
        ii. is configured to elute the therapeutic substance into tissue of the ET;
    (b) providing an intermittent gas pathway between a lumen of the ET and the nasopharynx using the endoluminal implant; and
    (c) eluting the therapeutic substance into the tissue of the ET that is adjacent to the endoluminal implant.

2. The method of claim 1, wherein the endoluminal implant further comprises:
   (a) a valve in fluid communication with the lumen of the ET, wherein the valve comprises:
      i. a first valve portion; and
      ii. a second valve portion;
   (b) a first connector portion connected with the first valve portion to couple the endoluminal implant to adjacent cartilage; and
   (c) a second connector portion connected with the second valve portion to further couple the implant to tensor villi palatine or levator villi palatine muscles.

3. The method of claim 2, wherein the first connector portion comprises a first tether configured to span across the adjacent cartilage and compress mucosa in the ET to secure the first valve portion to the adjacent cartilage.

4. The method of claim 2, wherein the valve is configured to modulate opening of the ET during swallowing due to movement of the tensor villi palatine or the levator villi palatine muscles.

5. The method of claim 1, wherein the endoluminal implant comprises a lumen.

6. The method of claim 5, wherein the lumen of the endoluminal implant contains the therapeutic substance.

7. The method of claim 6, wherein the therapeutic substance is configured to elute over time from the lumen of the endoluminal implant into the tissue of the ET.

8. The method of claim 1, wherein the therapeutic substance is configured to encourage tissue growth, limit stenosis of the ET and combinations thereof.

9. The method of claim 5, wherein the lumen of the endoluminal implant comprises a woven graft, expandable mesh or preformed lumen.

10. An endoluminal implant for providing a gas pathway between a nasopharynx and Eustachian Tube (ET) of a patient and introducing a therapeutic substance into the ET of the patient, the endoluminal implant comprising:
    (a) a lumen dimensioned for insertion into the ET, the lumen containing the therapeutic substance;
    (b) a valve in fluid communication with the lumen, the valve having a first valve portion and a second valve portion;
    (c) a first connector portion connected with the first valve portion to tether the implant to cartilage adjacent to the ET;
    (d) a second connector portion connected with the second valve portion to tether the implant to adjacent tensor villi palatine or the levator villi palatine muscles;
    wherein the first connector portion comprises a first tether configured to span across the cartilage and compress mucosa in a lumen of the ET to secure the first valve portion with the cartilage.

11. The endoluminal implant of claim 10, wherein the valve is configured to modulate the opening of the ET during swallowing due to movement of the tensor villi palatine or the levator villi palatine muscles.

12. The endoluminal implant of claim 10, wherein the therapeutic substance is configured to elute over time from the lumen of the endoluminal implant.

13. The endoluminal implant of claim 10, wherein the therapeutic substance is configured to encourage tissue growth, limit stenosis of the ET and combinations thereof.

14. The endoluminal implant of claim 10, wherein the lumen of the endoluminal implant comprises a woven graft, expandable mesh or preformed lumen.

15. An endoluminal implant for providing a gas pathway and introducing a therapeutic substance in the middle ear region of a patient, the endoluminal implant comprising an elongated spring member dimensioned for insertion into a Eustachian tube (ET) of the patient, wherein the elongated spring member comprises the therapeutic substance and is configured to:
    (a) apply a force to modulate an opening in a gas pathway in communication with a lumen of a Eustachian Tube (ET) and a nasopharynx of the patient; and
    (b) deliver the therapeutic substance to adjacent tissue.

16. The endoluminal implant of claim 15, wherein the therapeutic substance is embedded on the spring member, coated on the spring member or combinations thereof.

17. The endoluminal implant of claim 15, wherein the therapeutic substance is configured to encourage tissue growth, limit stenosis of the ET and combinations thereof.

18. The endoluminal implant of claim 15, wherein the therapeutic substance is configured to cause tissue to grow into or over the elongated spring member.

19. The endoluminal implant of claim 15, wherein the implant is configured to cause tissue ingrowth.

20. The endoluminal implant of claim 15, wherein the elongated spring member defines an elongated clam shell configuration.

* * * * *